(12) United States Patent
Manalis et al.

(10) Patent No.: US 8,312,763 B2
(45) Date of Patent: Nov. 20, 2012

(54) METHOD AND APPARATUS FOR TRAPPING SINGLE PARTICLES IN MICROFLUIDIC CHANNELS

(75) Inventors: Scott R. Manalis, Cambridge, MA (US);
Andrea K. Bryan, Allston, MA (US);
Philip Dextras, Cambridge, MA (US);
Thomas P. Burg, Goettingen (DE);
William H. Grover, Medford, MA (US);
Yao-Chung Weng, Cambridge, MA (US); Sungmin Son, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 395 days.

(21) Appl. No.: 12/587,898

(22) Filed: Oct. 14, 2009

(65) Prior Publication Data
US 2010/0154535 A1 Jun. 24, 2010

Related U.S. Application Data

(60) Provisional application No. 61/105,619, filed on Oct. 15, 2008.

(51) Int. Cl.
*G01N 15/06* (2006.01)
(52) U.S. Cl. ............ 73/61.72; 73/61.71; 73/61.73
(58) Field of Classification Search ............ 73/61.71, 73/61.73
See application file for complete search history.

(56) References Cited

U.S. PATENT DOCUMENTS

| | | | |
|---|---|---|---|
| 2002/0058332 A1* | 5/2002 | Quake et al. | 435/288.3 |
| 2008/0194012 A1* | 8/2008 | Lee et al. | 435/287.1 |
| 2009/0014360 A1* | 1/2009 | Toner et al. | 209/208 |

* cited by examiner

*Primary Examiner* — Hezron E Williams
*Assistant Examiner* — Paul West
(74) *Attorney, Agent, or Firm* — Mark Rodgers

(57) ABSTRACT

Methods and apparatus for improving measurements of particle or cell characteristics, such as mass, in Susspended Microchannel Resonators (SMR's). Apparatus include in particular designs for trapping particles in SMR's for extended measurement periods. Methods include techniques to provide differential measurements by varying the fluid density for repeated measurements on the same particle or cell.

4 Claims, 8 Drawing Sheets

METHOD AND APPARATUS FOR TRAPPING SINGLE PARTICLES IN MICROFLUIDIC CHANNELS

RELATED APPLICATIONS

This application claims priority to provisional application Ser. No. 61/105,619 filed Oct. 15, 2008, the contents of which are incorporated herein by reference.

FEDERALLY SPONSORED RESEARCH

National Institutes of Health (NIH) R01GM085457 Institute for Collaborative Biotechnologies from the U.S. Army Research Office

BACKGROUND OF THE INVENTION

This invention relates to methods and apparatus for measuring a property such as mass, size or density of target particles, and more particularly to such measurements using a Suspended Microchannel Resonator (SMR).

Precision measurements of nanometer- and micrometer-scale particles, including living cells, have wide application in pharmaceuticals/drug delivery, disease studies, paints and coatings, foods, and other major industries and fields of research. This need is growing due to the expanding use of particulate engineering across these industries, to emerging nano- and micro-particle manufacturing techniques, to the need to better understand and treat diseases, and to recent regulations governing quality control in the pharmaceutical industry.

A variety of particle sizing and counting techniques, such as light scattering, Coulter Counters and others are known in the art. These techniques are embodied in commercial instruments and are used in industrial, medical, and research applications. Although such techniques have proven utility, they have limitations, which limit their applicability. Relatively recently, particle detection and measurement based on the use of SMR's has been developed, and shows promise of going beyond some of the limitations of conventional techniques. The SMR uses a fluidic microchannel embedded in a resonant structure, typically in the form of a cantilever or torsional structure. Fluids, possibly containing target particles are flowed through the sensor, and the contribution of the flowed material to the total mass within the sensor causes the resonance frequency of the sensor to change in a measurable fashion. SMR's are typically microfabricated MEMS devices. Using microfabricated resonant mass sensors to measure fluid density has been known in the literature for some time [P. Enoksson, G. Stemme, E. Stemme, "Silicon tube structures for a fluid-density sensor", Sensors and Actuators A 54 (1996) 558-562]. However, the practical use of resonant mass sensors to measure properties of individual particles and other entities suspended in fluid is relatively recent, as earlier fluid density sensors had insufficient resolution to detect and measure individual particles at the micron and submicron scale.

In a body of work by common inventors and owned by the assignee of the current application, miniaturization and improvement of several orders of magnitude in mass resolution has been demonstrated. Development in the microfabrication recipes, the fluidics design, and measurement techniques are described in a number of co-pending patent applications and scientific publications. In particular U.S. patent applications, Ser. Nos. 11/620,320, 12/087,495, and 12/305,733 are particularly relevant and are incorporated by reference in their entirety. Also of relevance is a publication by some of the current inventors, [T. P. Burg, M. Godin, S. M. Knudsen et al., "Weighing of biomolecules, single cells and single nanoparticles in fluid," Nature 446 (7139), 1066-1069 (2007)] By using the microfabrication techniques described in the references, SMR sensors have been fabricated with mass resolution of less than 1 femtogram ($10^{-15}$ g). This resolution is sufficient to detect and measure the mass of individual particles in the range of several nanometers up to many microns in size, including living cells.

Despite the progress made in SMR design and measurement techniques, further improvements are desirable, particularly for applications involving small numbers of, or individual, particles or cells. Signal to noise can still limit the application of the technique, and both for better signal characteristics as well as expanding the range of applications, it is desirable to control the positioning of particles within the resonator. In addition it is highly desirable to measure the density of a particle, as discussed in the earlier references for characterization purposes. The present invention discloses apparatus and methods for improved particle measurement utilizing SMR's.

SUMMARY OF THE INVENTION

In one embodiment, the invention is an SMR with a main channel and an additional channel with it's own pressure controlled port. The additional channel is in fluid communication with main SMR channel and has a particle trap. The pressure can be controlled in the additional channel to either cause flow from the main channel into the trap to trap a particle, or to cause flow away from the trap into the main channel to release the particle.

In various aspects of the embodiment, the trap may be a slit or a sieve of any orientation, but preferably oriented horizontally or vertically to the plain of the SMR. In typical implementations, the channel dimensions are in the range of 10 20 microns in cross section, while the trap dimensions are on the order of one micron.

In other embodiments, one or more posts leaving small gaps, preferably on the order of a micron are disposed across a region of the flow channel to trap a particle.

In other embodiments the invention is a method of measuring the density of a particle by measuring the particle's effect on the resonant behavior of SMR's in fluid carriers of differing fluid densities. In one aspect, two (or more) SMR's are plumbed in series. A target particle is flowed through a first SMR in a fluid of a first density and the resonant effect is measured. In between the first and a second SMR, the carrier fluid density is changed and the resonant effect is measured on the second SMR with the particle in the modified density carrier, and the density is computed from the two measurements.

In another aspect using an SMR with a particle trap, a particle is trapped in the SMR, allowing the carrier fluid density to be changed with the particle remaining trapped, enabling difference measurements as above. A preferred technique to change carrier density is to mix in fluid with a different density with the first density fluid between measurements.

In another embodiment, an SMR is used as a Coulter Counter. Electrodes are placed in two electrolyte reservoirs connected by the micro channel of an SMR. Current is measured between the reservoirs. A particle that enters the SMR will reduce the current level by an amount that depends on the particle's volume. The same particle introduced into the SMR carried by the electrolyte will affect the resonant behavior proportional to their total buoyant mass. Thus particle density may be directly calculated.

BRIEF DESCRIPTION OF THE DRAWINGS

The invention will be better understood by referring to the following figures.

DETAILED DESCRIPTION OF THE INVENTION

The embodiments described herein are improved apparatus and methods that can be implemented using the microfabrication techniques and fluidics disclosed in the documents referenced and other publications available at the time the invention was made. Since those aspects of the invention do not contribute to the novelty, they are not described in detail. For instance novel versions of the SMR's may be produced with mask changes in the microfabrication process. Similarly the fluidics, data acquisition, and data processing steps can be accomplished with straightforward changes to set-ups previously disclosed. The novelty of the current invention lies in the arranging of the physical SMR geometries and measurement steps to achieve significantly improved results. Also the term particle is interchangeably used in this application to mean any particulate substance, including cells, and particularly live cells in a suitable carrier fluid. Thus particular embodiments may be described in terms of cells and others in terms of particles, but it is to be understood that no embodiments herein disclosed are restricted to a particular type of particle.

Figure 1:
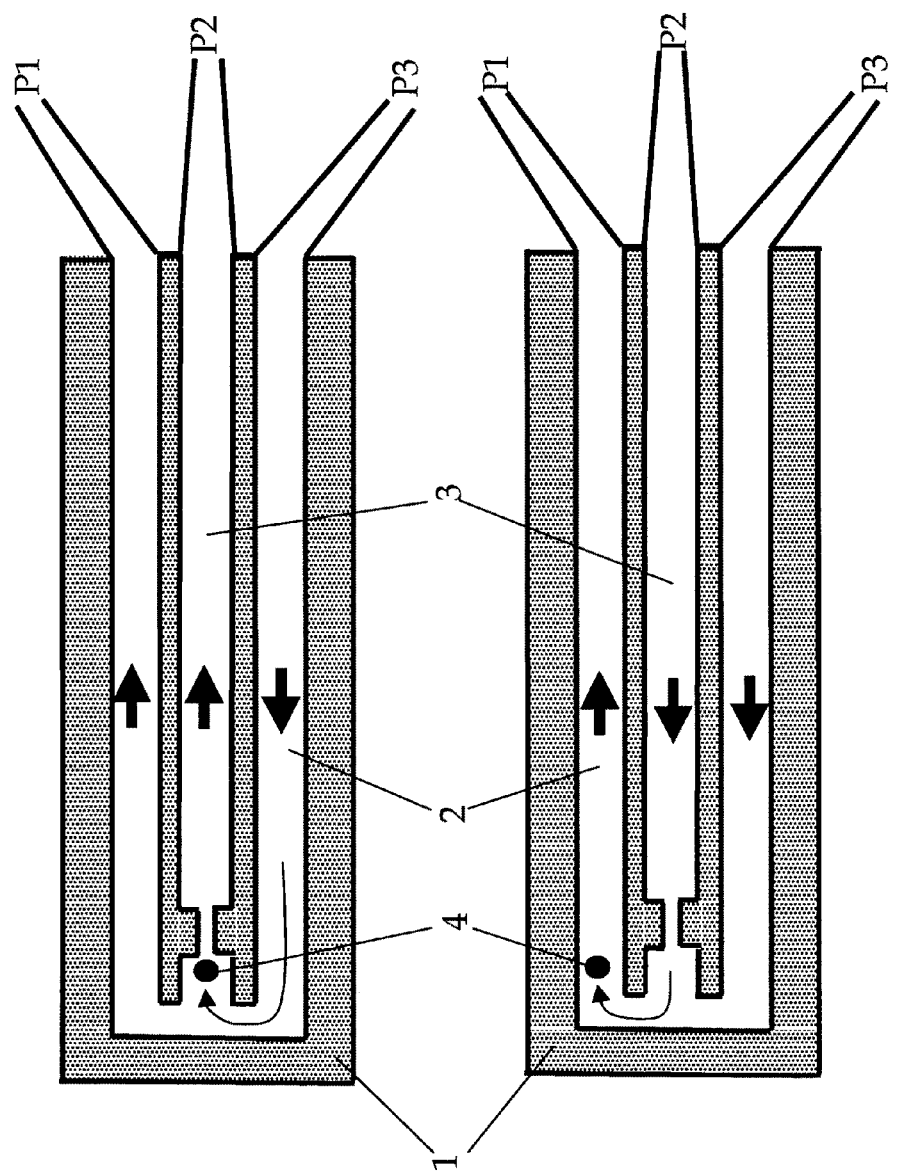
FIG. 1 is a schematic illustration of a Suspended Microchannel Resonator configured with an additional channel and particle trap.

Referring to FIG. 1, a typical cantilever shaped SMR 1 has a microfluidic channel 2 with ports P1 and P3, whose pressure is controllable to cause fluid flow through the channel 2. A novel additional channel 3, which connects with channel 2, with it's own Port P2, is added for this embodiment of the invention. The pressure of Port P2 can be adjusted relative to P1 and P3 to either divert flow into channel 3, or cause flow from channel 3 into channel 2. Thus when a particle 4 is introduced into the carrier fluid in channel 2, the pressure at P3 may be adjusted to cause particle 4 to divert into channel 3

As shown, channel 3 may include a trap geometry smaller than the channel dimensions, sized to trap particles in a size range of interest. Thus particle 4 may be held within the SMR 1 for a long period, which enables a wide variety of potential applications which will be described herein and in other co-pending applications. When desired, the pressure at P3 may be adjusted to push particle 4 away from the trap and into the flow in channel 2 carrying the particle out of the SMR 1. This the novel SMR provides precise trapping control without the need to back flush the SMR to remove the particle as is the case in previously disclosed SMR particle traps.

Figure 2:
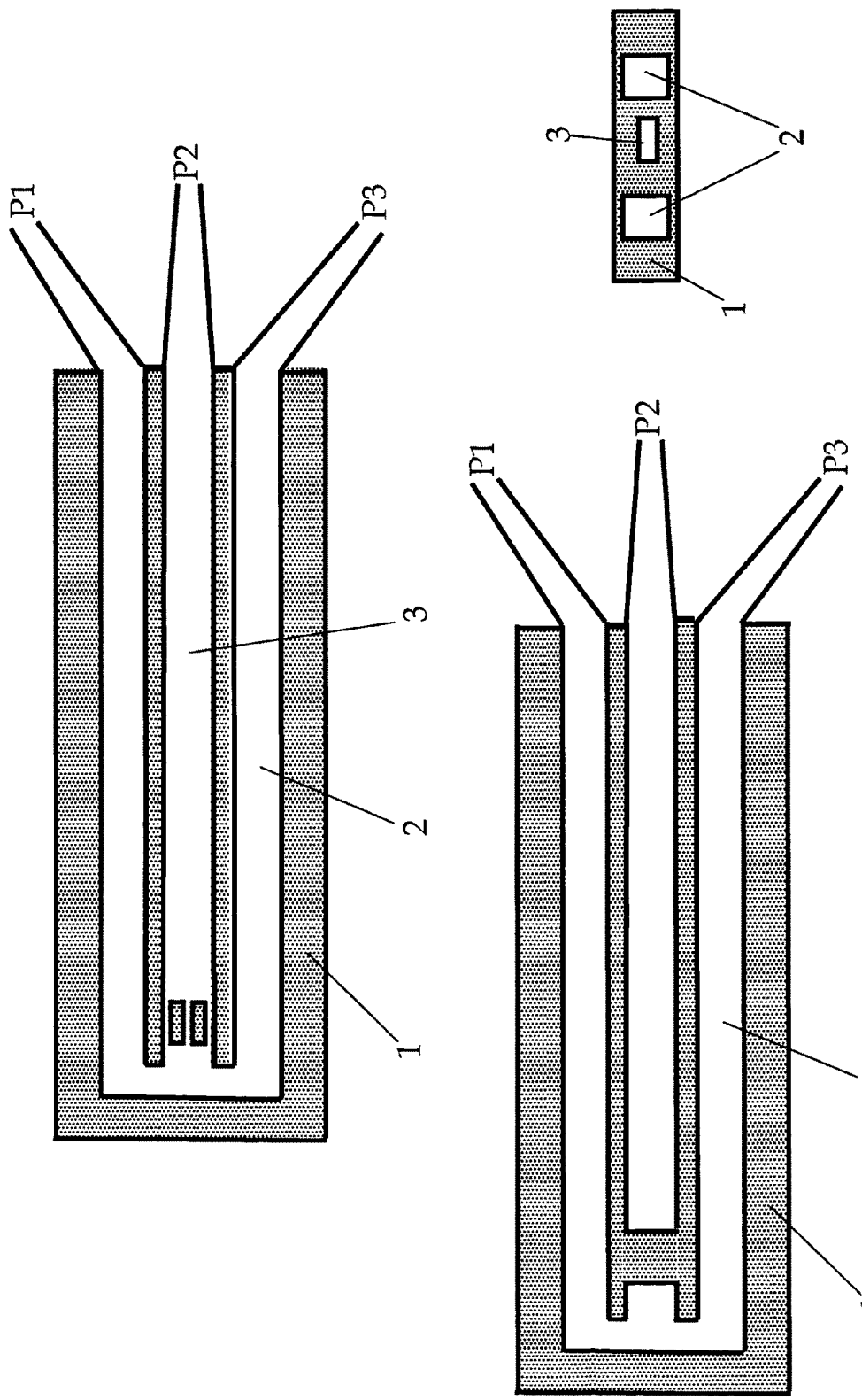
FIG. 2 depicts other trap geometries compatible with the SMR of FIG. 1.

FIG. 1 depicts the trap as a vertical slit. FIG. 2 shows other trap arrangements such as a vertical sieve and a horizontal slit. Other possible shapes and orientations for traps would also work from a functional standpoint as long as it is sized appropriately. However the micro fabrication processes used favor rectilinear features, which are oriented either vertically or horizontally to the plane of the SMR, so such arrangements are preferred. Although dimensions of the channels and traps may vary as needed within the microfabrication process design rules, channel cross section dimensions on the order of 10-20 microns, and trap dimensions with openings on the order of 1 micron have been found to be useful, particular for cells. For the case of a cantilever shaped SMR, the most sensitive measurement region is near the free end, so the traps and channels should be arranged accordingly as shown. However one skilled in the art will recognize that there is latitude in the precise placement of the structures. For other SMR geometries, the trap should be placed near the measurement sensitive region as appropriate for the geometry.

Figure 3:
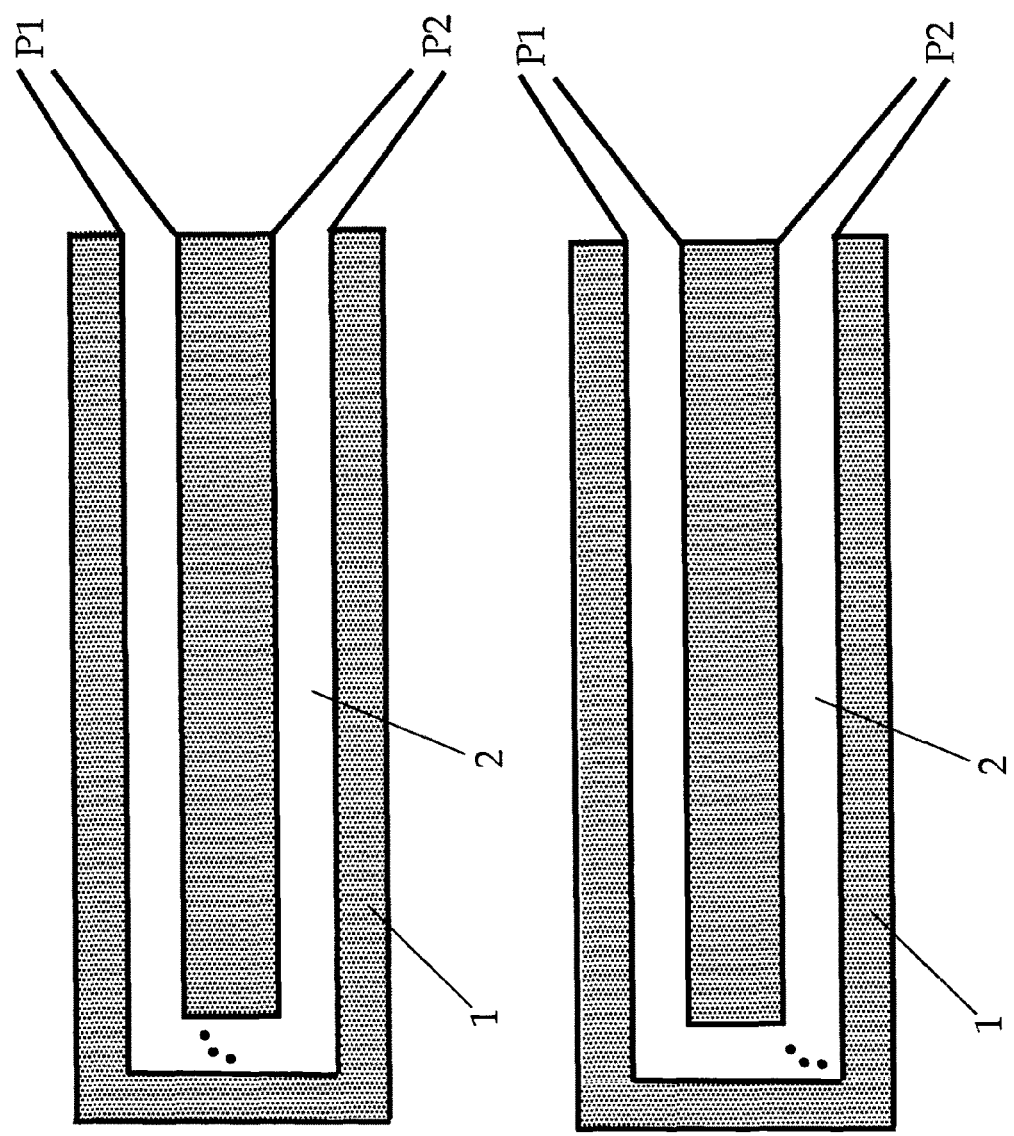
FIG. 3 is a schematic illustration of post traps according to the invention.

FIG. 3 shows another novel trap geometry used in a conventional single channel 2, two port SMR 1. In this embodiment the trap consists of one or more posts spanning a dimension of channel 2. The posts are advantageous because it's harder for softer particles such as cells to be pushed through by the applied pressure.

Figure 4:
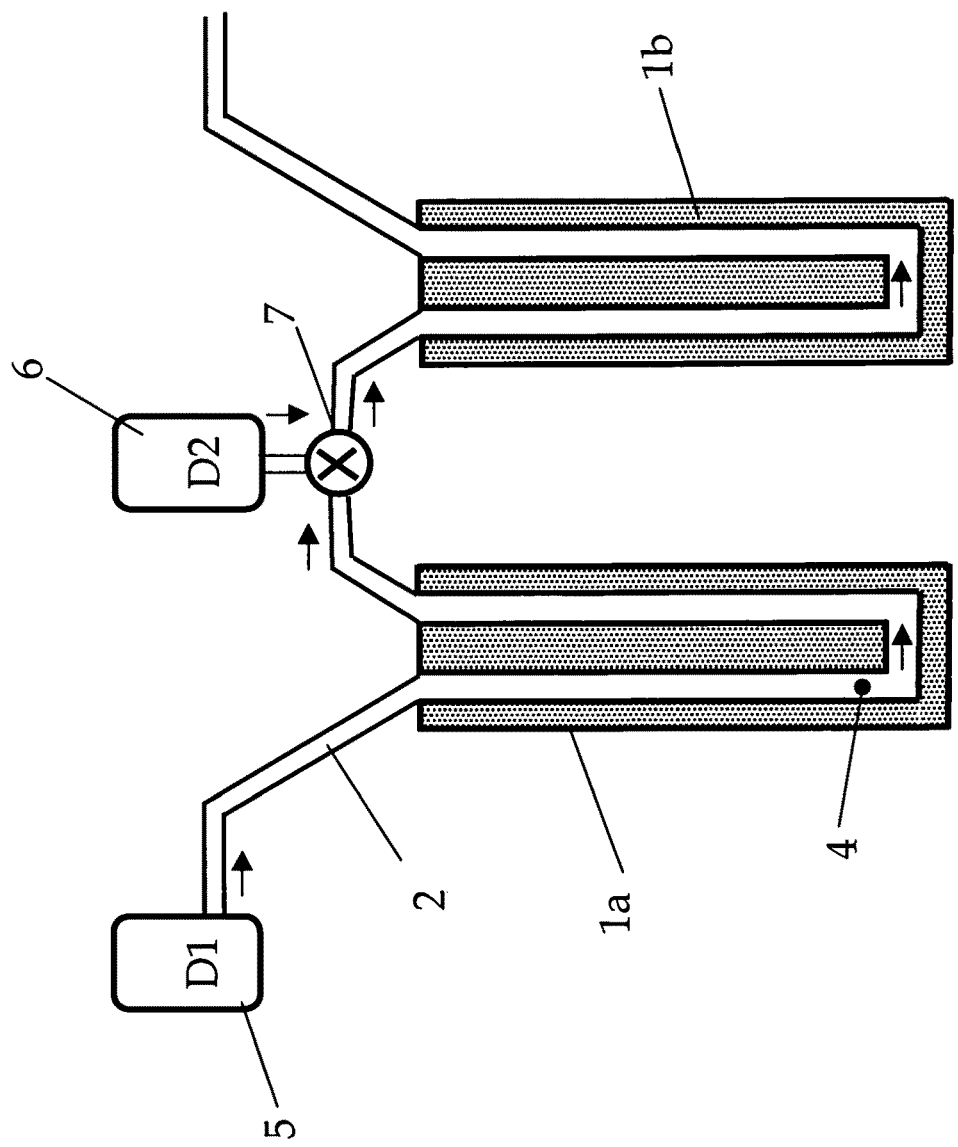
FIG. 4 is schematic of a set-up utilizing serial SMR's and a capability to change carrier fluid density between the SMR's.

Trapping a particle has many obvious measurement advantages, such as allowing multiple measurements with the particle in a repeatable location, providing benefits such as the ability to average measurements, or observe particle characteristics change over time. Another desired improvement is to take data in a fashion that allows density to be measured. A method to accomplish this measurement is shown in FIG. 4. Two (or more) SMR's 1a and 1b are plumbed serially such that fluid flow passes through them sequentially. A fluid of a first density 5 is introduced into channel 2 along with particle (or cell) 4. A resonator measurement is made while particle 4 is in SMR 1a. Between the resonators, the fluid density is changed. A preferable technique to change the fluid density is to mix at 7 a fluid 6 of a different density at least one known ratio, thus providing a fluid flowing in SMR 1b of a known different density than flows in 1a. When particle 4 is in 1b, the resonant measurement is repeated. Assuming SMR's 1a and 1b are nearly identical or any disparities are calibrated out, the measurement of the buoyant mass from each cantilever can be used to determine the particle's density, volume and absolute mass (as depicted in FIG. 5).

Figure 5:
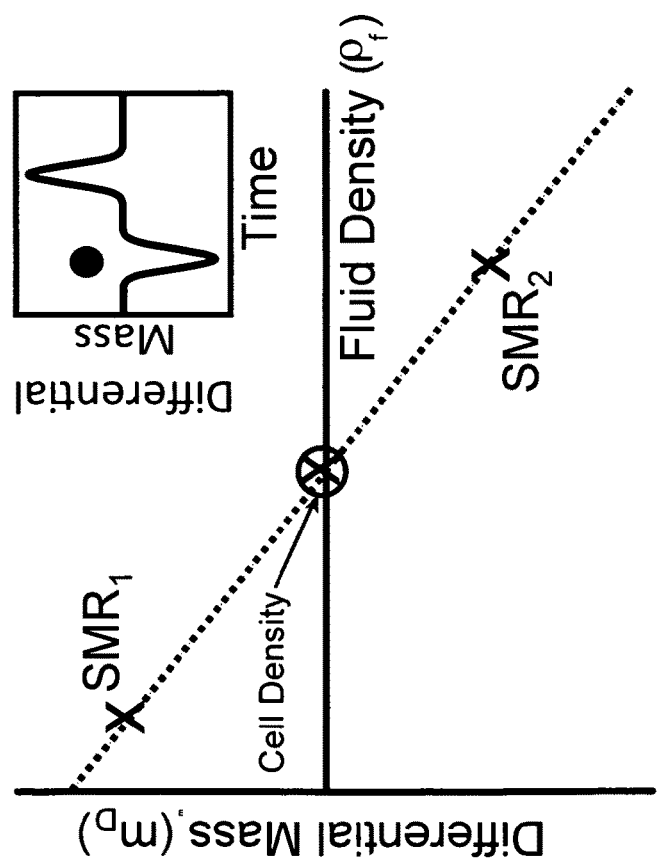
FIG. 5 is a graph showing sample data obtainable from the set-up of FIG. 4.

Sample data obtained from a set-up such as in FIG. 4 is shown in FIG. 5 for the case where the particles are cells. FIG. 5 shows that by measuring the cell's buoyant mass in solutions of two different densities (in the case shown, the cell has either a positive or negative buoyant mass), it is possible to calculate its density, total mass, and volume.

Figure 6:
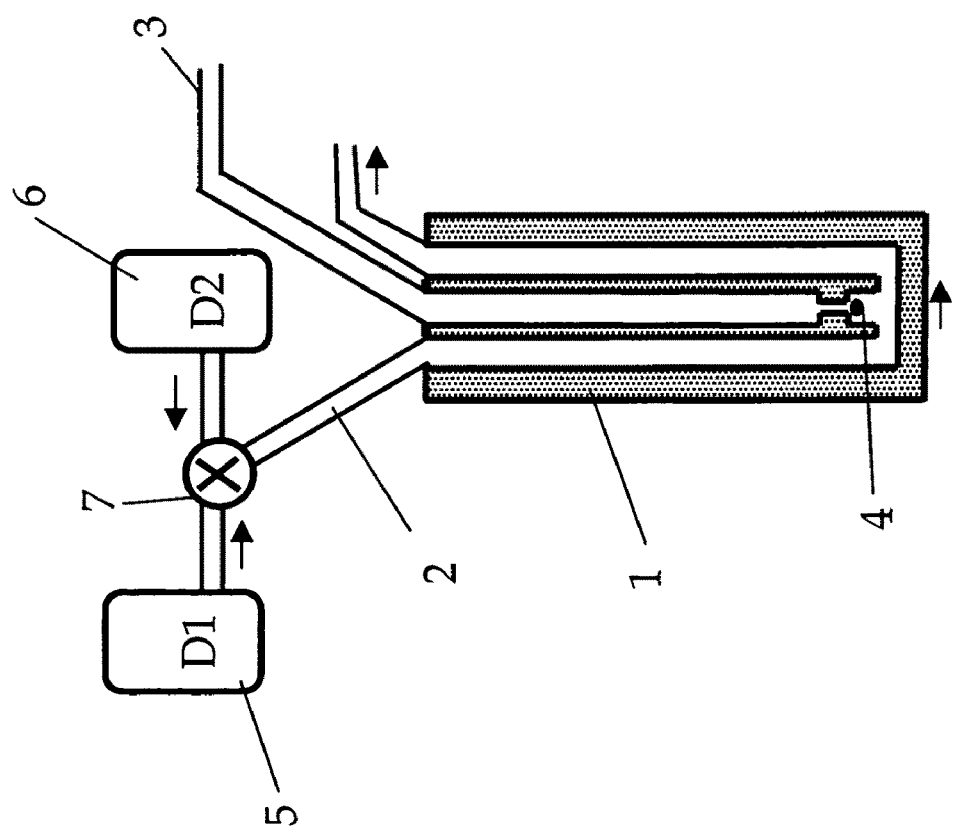
FIG. 6 is schematic of a set-up utilizing an SMR with a particle trap and a capability to change carrier fluid density between measurements.
Figure 7:
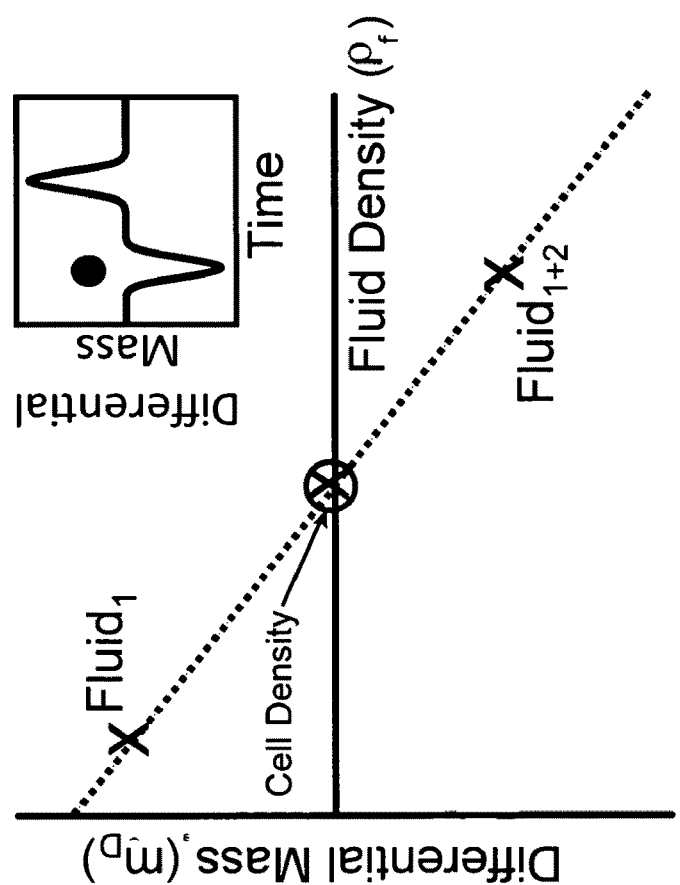
FIG. 7 is a graph showing sample data obtainable from the set-up of FIG. 6.

FIG. 6 depicts another set-up for practicing the buoyant mass differential fluid density method, utilizing an SMR 1 with a trap. The particle 4 is trapped, and then measurement (s) are made at a first fluid density 5, the density is changed and the measurements are repeated. Again the mixing at 7 of Fluid 6 with fluid 5 is a preferred technique to change the density of the fluid in channel 2. FIG. 7 shows corresponding sample results from this set-up to the results in FIG. 5

Figure 8:
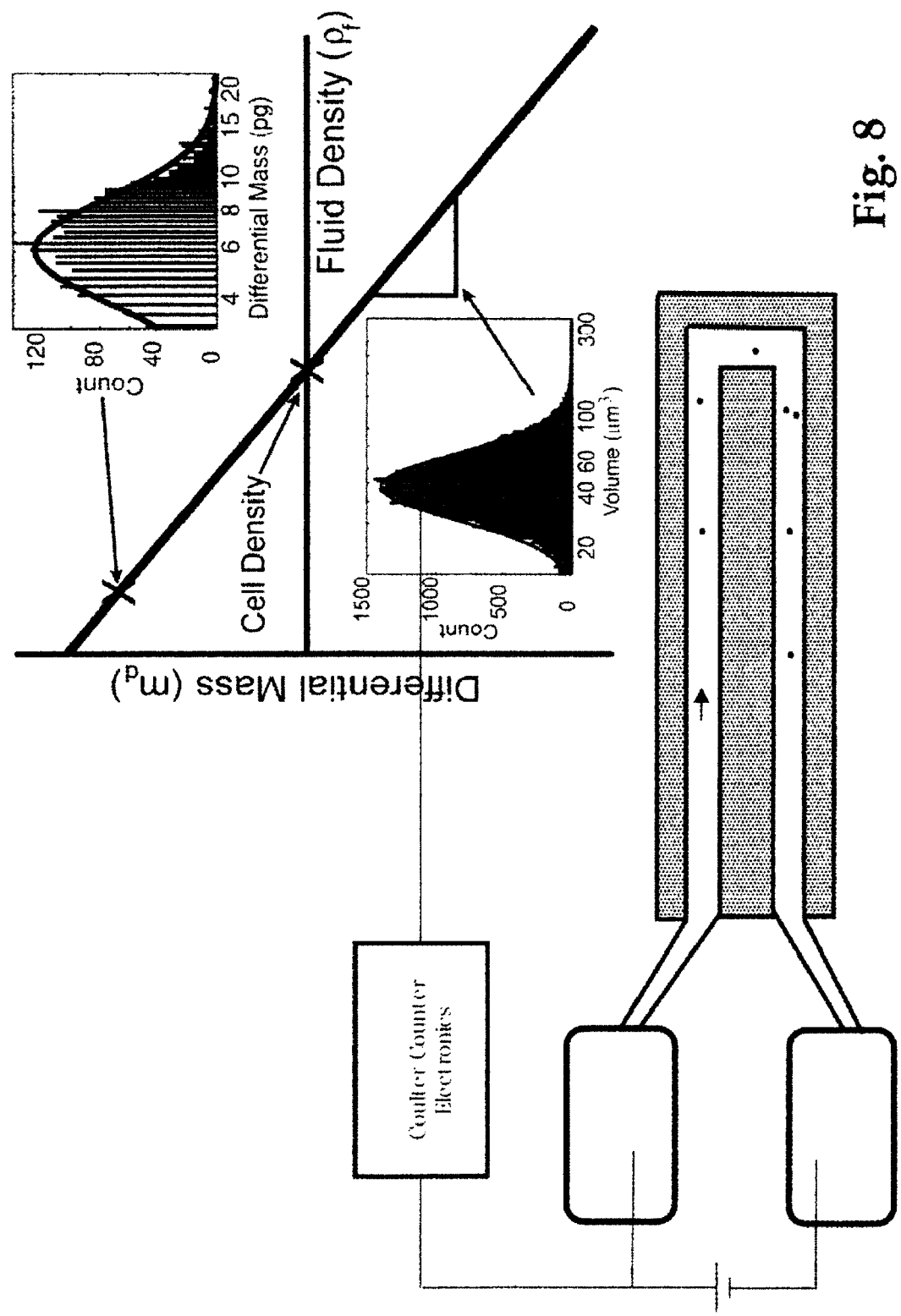
FIG. 8 is a diagram of a set-up where an SMR is used as the bypass channel for a coulter counter.

Another novel SMR set-up for measuring density is shown in FIG. 8. Two reservoirs containing an electrolyte have electrodes placed in them. The electrodes are connected to Coulter Counter electronics, known in the art. The fluidics channel of an SMR is plumbed as the Coulter bypass channel as shown. Particles, in this case cells, introduced into the SMR will have their total buoyant mass measured by their effect on the resonant behavior. The same particles will have their total volume measured by the Coulter effect. Thus particle density can be directly calculated as shown in the Figure.

What is claimed is:

1. A Suspended Microchannel Resonator (SMR), comprising;
    an oscillating substrate, with at least one fixed end and a region of high sensitivity away from the fixed end oscillated at or near resonance during operation; and,
    a microfluidic system built into the substrate, comprising;
    a first fluid channel disposed between an inlet and an outlet port,
    a second channel with a separately controlled port, one end of the second channel in communication with the first channel at or near the region of high sensitivity; and
    a particle trap disposed in the second channel at or near the region of high sensitivity, wherein;
    the pressure differential between the first channel ports are adjustable to cause flow from port to port, and the pressure of the second channel port is adjustable to cause at least one of diverted flow from the first channel into the trap to trap a particle or push flow away from the trap into the first channel to release the particle, the particle's presence detectable by its effect on the resonant frequency of the SMR, allowing for trapping of the particle in the second trapping channel to measure characteristics of the particle determined from its effect on the resonant frequency while trapped.

2. The SMR of claim 1 wherein the channel dimensions are between 10 and 20 microns, and the trap dimensions are on the order of one micron.

3. The SMR of claim 1 wherein the particle trap is one of a group comprising;
    a slit,
    a sieve.

4. The SMR of claim 3 wherein the trap is oriented at least one of vertically or horizontally to a plain of the resonator.

* * * * *